(12) United States Patent
Smail et al.

(10) Patent No.: US 11,832,868 B2
(45) Date of Patent: Dec. 5, 2023

(54) MEASURING THE PRESENCE TIME OF A CATHETER IN A PATIENT DURING A MEDICAL PROCEDURE

(71) Applicant: Boston Scientific Scimed Inc., Maple Grove, MN (US)

(72) Inventors: El Yacine Alex Smail, Vaudreuil-Dorion (CA); Chadi Harmouche, Saint-Laurent (CA)

(73) Assignee: Boston Scientific Scimed, Inc., Maple Grove, MN (US)

(*) Notice: Subject to any disclaimer, the term of this patent is extended or adjusted under 35 U.S.C. 154(b) by 437 days.

(21) Appl. No.: 17/122,487

(22) Filed: Dec. 15, 2020

(65) Prior Publication Data

US 2021/0228253 A1    Jul. 29, 2021

Related U.S. Application Data

(60) Provisional application No. 62/966,737, filed on Jan. 28, 2020.

(51) Int. Cl.
| | |
|---|---|
| A61B 18/02 | (2006.01) |
| A61B 34/00 | (2016.01) |
| G04F 10/00 | (2006.01) |
| A61B 18/00 | (2006.01) |

(52) U.S. Cl.
CPC .............. *A61B 18/02* (2013.01); *A61B 34/25* (2016.02); *G04F 10/00* (2013.01); *A61B 2018/0022* (2013.01); *A61B 2018/00345* (2013.01); *A61B 2018/00577* (2013.01); *A61B 2018/00678* (2013.01); *A61B 2018/00791* (2013.01); *A61B 2018/0212* (2013.01)

(58) Field of Classification Search
CPC .. A61B 2090/0814; A61M 2205/3368; A61M 2205/3372
See application file for complete search history.

(56) References Cited

U.S. PATENT DOCUMENTS

| 7,307,245 B2 | 12/2007 | Faries, Jr. et al. |
| 9,913,680 B2 | 3/2018 | Voegele et al. |
| 2009/0149932 A1* | 6/2009 | Thompson ............. A61B 18/08 607/113 |

FOREIGN PATENT DOCUMENTS

RU    2526968 C2    8/2014

* cited by examiner

*Primary Examiner* — Ronald Hupczey, Jr.
(74) *Attorney, Agent, or Firm* — Nelson Mullins Riley & Scarborough LLP

(57) ABSTRACT

A system including a controller to determine an in-body time of a medical device in a patient during a medical procedure. The controller to: receive signals from at least one temperature sensor; detect insertion of the medical device into the patient by one or more of determining the temperature of the medical device and determining the change of temperature of the medical device with respect to time; increment an in-body time counter to measure the in-body time of the medical device after detecting insertion of the medical device into the patient; detect that the medical device has been removed from the patient by determining that the change of temperature of the medical device with respect to time is negative; and stop incrementing the in-body time counter in response to detecting that the medical device has been removed.

20 Claims, 5 Drawing Sheets

MEASURING THE PRESENCE TIME OF A CATHETER IN A PATIENT DURING A MEDICAL PROCEDURE

CROSS REFERENCE TO RELATED APPLICATION

This application claims priority to Provisional Application No. 62/966,737, filed Jan. 28, 2020, which is herein incorporated by reference in its entirety.

TECHNICAL FIELD

The present invention relates to medical devices and methods for performing electrophysiology procedures. More specifically, the invention relates to devices and methods for monitoring the presence of a cryoablation catheter within a patient's body during a cryoablation procedure.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal, i.e., farthest from the user or operator, portion of the catheter and often at the tip of the catheter.

Various forms of energy can be used to ablate diseased heart tissue. These can include radio frequency (RF), cryogenics, ultrasound, and laser energy, to name a few. During a cryoablation procedure, with the aid of a guide wire, the distal tip of the catheter is positioned adjacent to targeted cardiac tissue, at which time energy is delivered to create tissue necrosis, rendering the ablated tissue incapable of conducting electrical signals. The dose of the energy delivered is a critical factor in increasing the likelihood that the treated tissue is permanently incapable of conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis while avoiding excessive energy leading to collateral tissue injury.

Atrial fibrillation (AF) is one of the most common arrhythmias treated using catheter ablation. In the earliest stages of the disease, paroxysmal AF, the treatment strategy involves isolating the pulmonary veins from the left atrial chamber. Recently, the use of techniques known as "balloon cryotherapy" catheter procedures to treat AF has increased. In part, this stems from the balloon cryotherapy's ease of use, shorter procedure times and improved patient outcomes. Despite these advantages, there remains needed improvement to further improve patient outcomes and to better facilitate real-time physiological monitoring of ablation procedures.

The goal of balloon cryotherapy is to completely isolate one or more pulmonary veins of the patient by creating circumferential transmural lesions around an ostium of the pulmonary vein being treated. During balloon cryotherapy, one or more cryogenic balloons are placed against the ostium of the pulmonary vein to occlude the pulmonary vein from blood flow. Pulmonary vein occlusion is typically a strong indicator that complete circumferential contact is achieved between the balloon and ostium of the pulmonary vein for optimal heat transfer during ablation. With the cryogenic balloons appropriately positioned to occlude the targeted tissue, e.g., the pulmonary vein, a cryogenic fluid (such as nitrous oxide, or any other suitable fluid) is delivered under pressure to an interior of the one or more cryogenic balloons. Using this method, the extremely frigid fluid causes necrosis of the targeted tissue, thereby rendering the ablated tissue incapable of conducting unwanted electrical signals.

SUMMARY

In Example 1, a system including a controller configured to determine an in-body time of a medical device in a patient during a medical procedure. The controller configured to: receive signals from at least one temperature sensor; detect insertion of the medical device into the patient by one or more of determining the temperature of the medical device and determining the change of temperature of the medical device with respect to time; increment an in-body time counter to measure the in-body time of the medical device after detecting insertion of the medical device into the patient; detect that the medical device has been removed from the patient by determining that the change of temperature of the medical device with respect to time is negative; and stop incrementing the in-body time counter in response to detecting that the medical device has been removed.

In Example 2, the system of Example 1, wherein the controller is configured to continue incrementing the in-body time counter if the controller determines that the system is in an ablation state and the temperature of the medical device is less than the threshold temperature.

In Example 3, the system of any one of Examples 1 and 2, wherein the controller is configured to continue incrementing the in-body time counter if the controller determines that the change of temperature of the medical device with respect to time is positive, and the system is in one of a thawing state, an idle state, and a ready state.

In Example 4, the system of any one of Examples 1-3, wherein the controller is configured to detect insertion of the medical device into the patient by comparing the temperature of the medical device to a threshold temperature, and if the temperature of the medical device is greater than the threshold temperature then the medical device has been inserted into the body of the patient.

In Example 5, the system of any one of Examples 1-4, wherein the controller is configured to detect insertion of the medical device into the patient by determining the change in temperature of the medical device with respect to time, and if the change of temperature is positive then the medical device has been inserted into the body of the patient.

In Example 6, the system of any one of Examples 1-5, wherein the controller is configured to detect insertion of the medical device into the patient by determining the change in temperature of the medical device with respect to time, and if the change of temperature is increasing at a rate that lies within a rate threshold range then the medical device has been inserted into the body of the patient.

In Example 7, the system of Example 1, wherein the controller is configured to detect insertion of the medical device into the patient by 1) comparing the temperature of the medical device to a threshold temperature that is between a room temperature of a room in which the medical procedure takes place and a body temperature of the patient and 2) determining the change of temperature is positive and/or the change in temperature is increasing at a rate that lies within a rate threshold range.

In Example 8, the system of any one of Examples 1-7, wherein the controller is configured to detect that the medical device has been removed from the patient by determining that the system is in an idle state or a ready state and the change of temperature of the medical device with respect to time is negative.

In Example 9, the system of any one of Examples 1-8, wherein the controller is configured to detect that the medical device has been removed from the patient by determining that the system has completed an ablation state and the change of temperature of the medical device with respect to time is negative.

In Example 10, the system of any one of Examples 1-9, comprising a graphical display configured to display the in-body time.

In Example 11, the system of Examples 10, wherein the graphical display displays the in-body time in real-time, as the in-body time counter is incremented.

In Example 12, the system of any one of Examples 10 and 11, wherein the graphical display displays the total in-body time after the controller has stopped incrementing the in-body time counter.

In Example 13, the system of any one of Examples 1-12, wherein the medical device is a catheter configured to be inserted into the patient.

In Example 14, the system of Example 13, wherein the catheter includes the at least one temperature sensor which is configured to measure the temperature of the catheter.

In Example 15, the system of any one of Examples 1-14, wherein the controller is configured to increment the in-body time counter at least once per second.

In Example 16, a method of determining an in-body time of a medical device in a body of a patient during a medical procedure. The method includes: providing the medical device outside the body of the patient such that a temperature of the medical device is less than a threshold temperature that is between a room temperature of a room in which the medical procedure takes place and a body temperature of the patient; detecting insertion of the medical device into the patient by one or more of measuring the temperature of the medical device and measuring the change of temperature of the medical device with respect to time; incrementing an in-body time counter to measure the in-body time of the medical device after detecting insertion of the medical device into the patient; detecting that the medical device has been removed from the patient by determining that the change of temperature of the medical device with respect to time is negative; stopping the incrementing of the in-body time counter in response to detecting that the medical device has been removed; and displaying the in-body time on the graphical display.

In Example 17, the method of Example 16, comprising: determining that a system is in an ablation state and the temperature of the medical device is less than the threshold temperature; and continuing the incrementing of the in-body time counter.

In Example 18, the method of Example 16, comprising: determining the change of the temperature of the medical device with respect to time is positive during one of a thawing state, an idle state, and a ready state of a system; and continuing the incrementing of the in-body time counter.

In Example 19, the method of Example 16, wherein detecting insertion of the medical device into the patient comprises comparing the temperature of the medical device to the threshold temperature, and if the temperature of the medical device is greater than the threshold temperature then the medical device has been inserted into the body of the patient.

In Example 20, the method of Example 16, wherein detecting insertion of the medical device into the patient comprises determining the change in temperature of the medical device with respect to time, and if the change of temperature is positive and/or the change in temperature is increasing at a rate that lies within a rate threshold range then the medical device has been inserted into the body of the patient.

In Example 21, the method of Example 16, wherein detecting insertion of the medical device into the patient comprises comparing the temperature of the medical device to the threshold temperature and determining the change in temperature of the medical device with respect to time, wherein 1) if the temperature of the medical device is greater than the threshold temperature and 2) the change of temperature is positive and/or the change in temperature is increasing at a rate that lies within a rate threshold range then the medical device has been inserted into the body of the patient.

In Example 22, the method of Example 16, wherein incrementing the in-body time counter comprises incrementing the in-body time counter at least once per second.

In Example 23, the method of Example 16, wherein detecting that the medical device has been removed from the patient comprises determining that a system is in an idle state or a ready state after an ablation state and the change of temperature of the medical device with respect to time is negative.

In Example 24, the method of Example 16, wherein displaying the in-body time on the graphical display comprises displaying the in-body time in real-time as the in-body time counter is incremented.

In Example 25, the method of Example 16, wherein displaying the in-body time on the graphical display comprises displaying the total in-body time after the incrementing of the in-body time counter has been stopped.

In Example 26, a method of determining a presence time of a catheter in a body of a patient during a cryoablation procedure. The method comprising: providing the catheter outside the body of the patient such that a temperature of the catheter is less than a threshold temperature that is between a room temperature of a room in which the cryoablation procedure takes place and a body temperature of the patient; powering-up an intravascular catheter system and entering a ready state of the intravascular catheter system; inserting the catheter into the patient; detecting insertion of the catheter into the patient during the ready state of the intravascular catheter system by one or more of measuring the temperature of the catheter and measuring the change of temperature of the catheter with respect to time; incrementing an in-body time counter at least once per second to measure the in-body time of the catheter after detecting insertion of the catheter into the patient; determining that the intravascular catheter system is in an ablation state and the temperature of the catheter is less than the threshold temperature and, in response, continuing the incrementing of the in-body time counter; determining the change of the temperature of the catheter with respect to time is positive during one of a thawing state, an idle state, and a ready state of the intravascular catheter system and, in response, continuing the incrementing of the in-body time counter; detecting that the catheter has been removed from the patient by determining that the change of temperature of the catheter with respect to time is negative during an idle state and/or a ready state after the ablation state; stopping the incrementing of the in-body time counter in response to detecting that the catheter has been removed; and displaying the in-body time on the graphical display.

In Example 27, the method of Example 26, wherein detecting insertion of the catheter into the patient comprises comparing the temperature of the catheter to the threshold temperature, and if the temperature of the catheter is greater than the threshold temperature then the catheter has been inserted into the body of the patient.

In Example 28, the method of Example 26, wherein detecting insertion of the catheter into the patient comprises determining the change in temperature of the catheter with respect to time, and if the change of temperature is positive and/or the change in temperature is increasing at a rate that lies within a rate threshold range then the catheter has been inserted into the body of the patient.

In Example 29, the method of Example 26, wherein detecting insertion of the catheter into the patient comprises comparing the temperature of the catheter to the threshold temperature and determining the change in temperature of the catheter with respect to time, wherein 1) if the temperature of the catheter is greater than the threshold temperature and 2) the change of temperature is positive and/or the change in temperature is increasing at a rate that lies within a rate threshold range then the catheter has been inserted into the body of the patient.

In Example 30, the method of Example 26, wherein displaying the in-body time on the graphical display comprises displaying the in-body time in real-time as the in-body time counter is incremented.

In Example 31, the method of Example 26, wherein displaying the in-body time on the graphical display comprises displaying the total in-body time after the incrementing of the in-body time counter has been stopped.

In Example 32, an intravascular catheter system, comprising a catheter configured to be inserted into a body of a patient, the catheter including at least one temperature sensor configured to measure the temperature of the catheter, and a controller configured to determine an in-body time of the catheter in the body of the patient during a medical procedure. The controller configured to: receive signals from the at least one temperature sensor; detect insertion of the catheter into the patient by one or more of determining the temperature of the catheter and determining the change of temperature of the catheter with respect to time; increment an in-body time counter to measure the in-body time of the catheter after detecting insertion of the catheter into the patient; detect that the catheter has been removed from the patient by determining that the change of temperature of the catheter with respect to time is negative; and stop incrementing the in-body time counter in response to detecting that the catheter has been removed. The system also includes a graphical display configured to display the in-body time counter on the graphical display.

In Example 33, the system of Example 32, wherein the controller is configured to detect insertion of the catheter into the patient by one or more of 1) comparing the temperature of the catheter to a threshold temperature that is between a room temperature of a room in which the medical procedure takes place and a body temperature of the patient and 2) determining the change of temperature is positive and/or the change in temperature is increasing at a rate that lies within a rate threshold range.

In Example 34, the system of Example 32, wherein the controller is configured to detect that the catheter has been removed from the patient by determining that the intravascular catheter system is in an idle state or a ready state after an ablation state and the change of temperature of the catheter with respect to time is negative.

In Example 35, the system of Example 32, wherein the graphical display displays one or more of the in-body time in real-time as the in-body time counter is incremented and the total in-body time after the incrementing of the in-body time counter has been stopped While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
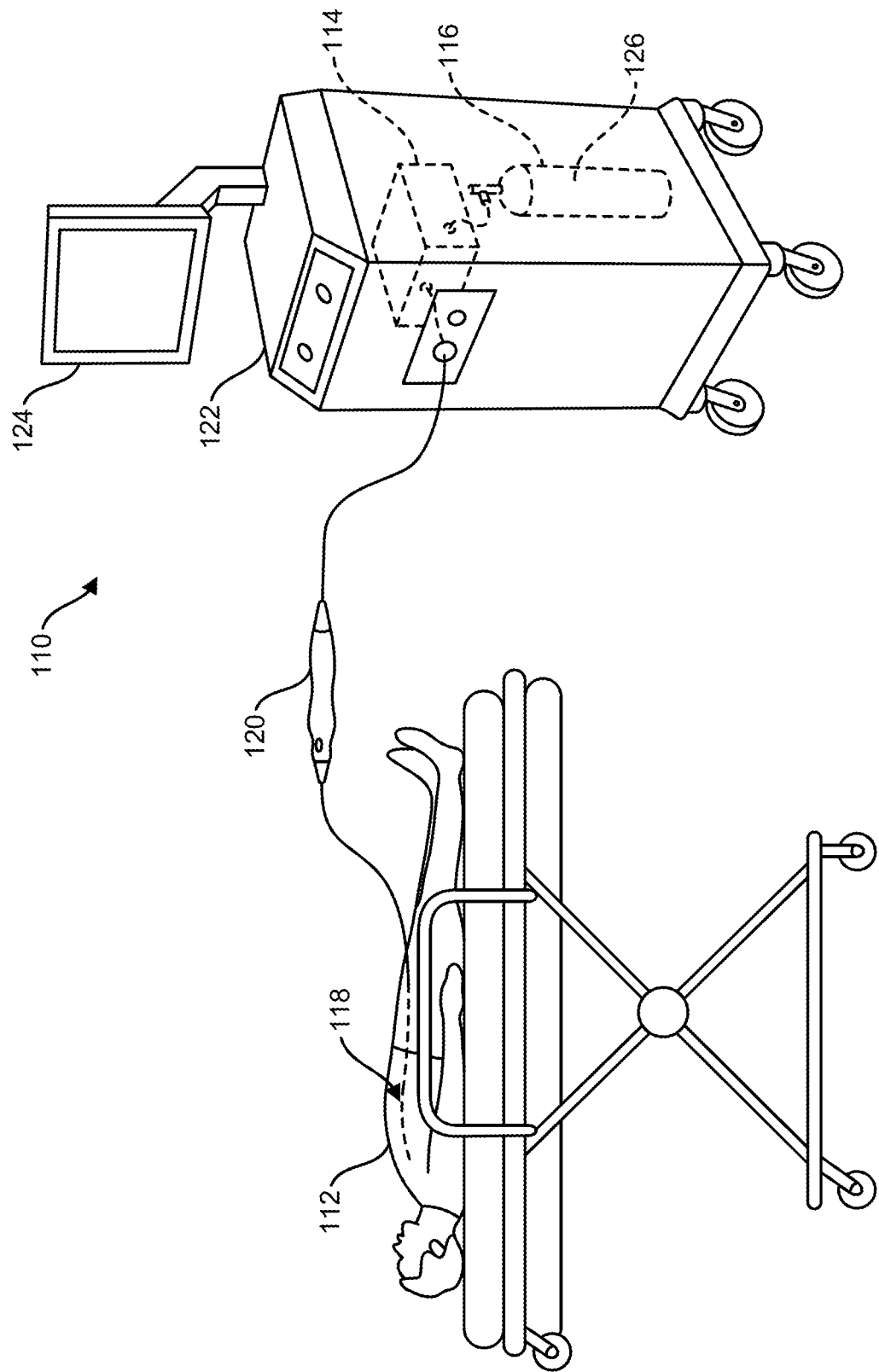
FIG. 1 is a simplified schematic side view illustrating a patient and an intravascular catheter system including a graphical display, according to embodiments of the disclosure.

While the disclosure is amenable to various modifications and alternative forms, specific embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the appended claims.

DETAILED DESCRIPTION

Embodiments of the present disclosure are described herein in the context of a graphical user interface, also referred to herein as a graphical display, for use within an intravascular catheter system. In embodiments, the graphical display provides an operator of the intravascular catheter system with information and data that can be used before, during, and after an ablation procedure, such as a cryoablation procedure. In embodiments, the graphical display provides an operator of the intravascular catheter system with a measurement of the in-body treatment time or duration of the medical procedure, as determined herein. In embodiments, the graphical display displays the measurement of the in-body treatment time or duration of the medical procedure, which can be used to more clearly define the medical procedure. In embodiments, the measurement of the in-body treatment time or duration of the medical procedure, as determined herein, can be used to improve planning of the medical procedure and/or reduce the cost of the medical procedure.

Those of ordinary skill in the art will realize that the following detailed description of the present disclosure is illustrative only and not intended to be in any way limiting. Other embodiments of the disclosure will readily suggest themselves to such skilled persons having the benefit of this disclosure.

Also, in the interest of clarity, not all routine features of the embodiments described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming but would nevertheless be a routine undertaking of engineering for those of ordinary skill in the art having the benefit of this disclosure.

Although the disclosure provided herein focuses mainly on cryogenics, it is to be understood that various other forms of energy can be used to ablate diseased heart tissue. These can include radio frequency (RF), ultrasound, and laser energy, as non-exclusive examples. The ideas of the present disclosure are intended to be effective with any or all of these and other forms of energy. Reference will now be made in detail to embodiments of the disclosure as illustrated in the accompanying drawings.

FIG. 1 is a simplified schematic side view illustrating a medical device or system 110 for use with a patient 112, which can be a human being or another animal, according to embodiments of the disclosure. Although the medical device 110 illustrated and described herein pertains to and refers to an intravascular catheter system 110, such as a cryogenic balloon catheter system, it is to be understood and appreciated that other types of medical devices or systems 110 can equally benefit by the teachings provided herein. For example, in certain non-exclusive alternative embodiments, the present disclosure can be equally applicable for use with other suitable types of ablation systems and/or other suitable types of catheter systems. Thus, reference herein to use as part of an intravascular catheter system is not intended to be limiting in any manner.

The design of the intravascular catheter system 110 can be varied. In embodiments, the intravascular catheter system 110 includes one or more of: a controller 114 (illustrated in dashed lines); a fluid source 116 (illustrated in dashed lines); a balloon catheter 118; a handle assembly 120; a control console 122; and a graphical display 124. It is to be understood that although FIG. 1 illustrates the structures of the intravascular catheter system 110 in particular positions, sequences, and/or order, these structures can be located in other suitable different positions, sequences, and/or order. Also, it is to be understood that the intravascular catheter system 110 can include fewer or more components than those illustrated and described herein.

In embodiments, the controller 114 is configured to monitor and control various processes of the ablation procedure. More specifically, the controller 114 can monitor and control release and/or retrieval of a cooling fluid 126, e.g., a cryogenic fluid, to and/or from the balloon catheter 118. The controller 114 can also control various structures that are responsible for maintaining and/or adjusting a flow rate and/or pressure of the cryogenic fluid 126 that is released to the balloon catheter 118 during the cryoablation procedure. In embodiments, the intravascular catheter system 110 delivers ablative energy in the form of cryogenic fluid 126 to cardiac tissue of the patient 112 to create tissue necrosis, rendering the ablated tissue incapable of conducting electrical signals. Additionally, in various embodiments, the controller 114 can control activation and/or deactivation of one or more other processes of the balloon catheter 118. Further, or in the alternative, the controller 114 can receive data and/or other information (hereinafter sometimes referred to as "sensor output") from various structures within the intravascular catheter system 110. In some embodiments, the controller 114 can receive, monitor, assimilate and/or integrate the sensor output, and/or any other data or information received from any structure within the intravascular catheter system 110 in order to control the operation of the balloon catheter 118. As provided herein, in various embodiments, the controller 114 can initiate and/or terminate the flow of cryogenic fluid 126 to the balloon catheter 118 based on the sensor output. Still further, or in the alternative, the controller 114 can control positioning of portions of the balloon catheter 118 within the body of the patient 112, and/or can control other suitable functions of the balloon catheter 118.

The fluid source 116 contains the cryogenic fluid 126, which is delivered to the balloon catheter 118 with or without input from the controller 114 during a cryoablation procedure. Once the ablation procedure has initiated, the cryogenic fluid 126 can be delivered to the balloon catheter 118 and the resulting gas, after a phase change, can be retrieved from the balloon catheter 118, and can either be vented or otherwise discarded as exhaust. Additionally, the type of cryogenic fluid 126 that is used during the cryoablation procedure can vary. In one non-exclusive embodiment, the cryogenic fluid 126 can include liquid nitrous oxide. However, any other suitable cryogenic fluid 126 can be used. For example, in one non-exclusive alternative embodiment, the cryogenic fluid 126 can include liquid nitrogen.

The design of the balloon catheter 118 can be varied to suit the specific design requirements of the intravascular catheter system 110. As shown, the balloon catheter 118 is inserted into the body of the patient 112 during the cryoablation procedure. In embodiments, the balloon catheter 118 can be positioned within the body of the patient 112 using the controller 114. Stated in another manner, the controller 114 can control positioning of the balloon catheter 118 within the body of the patient 112. Alternatively, the balloon catheter 118 can be manually positioned within the body of the patient 112 by a healthcare professional (also referred to herein as an "operator"). As used herein, a healthcare professional and/or an operator can include a physician, a physician's assistant, a nurse and/or any other suitable person and/or individual. In some embodiments, the balloon catheter 118 is positioned within the body of the patient 112 utilizing at least a portion of the sensor output that is received by the controller 114. For example, in various embodiments, the sensor output is received by the controller 114, which can then provide the operator with information regarding the positioning of the balloon catheter 118. Based at least partially on the sensor output feedback received by the controller 114, the operator can adjust the positioning of the balloon catheter 118 within the body of the patient 112 to ensure that the balloon catheter 118 is properly positioned relative to targeted cardiac tissue (not shown). While specific reference is made herein to the balloon catheter 118, as noted above, it is understood that another suitable type of medical device and/or catheter may be used.

The handle assembly 120 is handled and used by the operator to operate, position and control the balloon catheter 118. The design and specific features of the handle assembly 120 can vary to suit the design requirements of the intravascular catheter system 110. In the embodiment illustrated in FIG. 1, the handle assembly 120 is separate from, but in electrical and/or fluid communication with the controller 114, the fluid source 116, and the graphical display 124. In some embodiments, the handle assembly 120 can integrate and/or include at least a portion of the controller 114 within an interior of the handle assembly 120. It is to be understood that the handle assembly 120 can include fewer or additional components than those specifically illustrated and described herein.

In embodiments, the handle assembly 120 can be used by the operator to initiate and/or terminate the cryoablation process, e.g., to start the flow of the cryogenic fluid 126 to the balloon catheter 118 in order to ablate certain targeted heart tissue of the patient 112. In some embodiments, the controller 114 can override use of the handle assembly 120 by the operator. Stated in another manner, in some embodiments, based at least in part on the sensor output, the controller 114 can terminate the cryoablation process without the operator using the handle assembly 120 to do so.

The control console 122 is coupled to the balloon catheter 118 and the handle assembly 120. Additionally, in the embodiments illustrated in FIG. 1, the control console 122 includes at least a portion of the controller 114, the fluid source 116, and the graphical display 124. However, in alternative embodiments, the control console 122 can contain additional structures not shown or described herein. Still alternatively, the control console 122 may not include various structures that are illustrated within the control console 122 in FIG. 1. For example, in certain nonexclusive alternative embodiments, the control console 122 does not include the graphical display 124.

In some embodiments, the graphical display 124 is electrically connected to the controller 114. Additionally, the graphical display 124 provides the operator of the intravascular catheter system 110 with information and data that can be used before, during, and after the cryoablation procedure. For example, the graphical display 124 can provide the operator with information based on the sensor output, and any other relevant information that can be used before, during, and after the cryoablation procedure. The specifics of the graphical display 124 can vary depending upon the design requirements of the intravascular catheter system 110, or the specific needs, specifications, and/or desires of the operator.

In embodiments, the graphical display 124 is configured to provide static visual data and/or information to the operator. In addition, or in the alternative, the graphical display 124 can be configured to provide dynamic visual data and/or information to the operator, such as video data or any other data that changes over time, e.g., during an ablation procedure, as provided in greater detail herein. Further, in various embodiments, the graphical display 124 can include one or more colors, different sizes, varying brightness, etc., that may act as alerts to the operator. Additionally, or in the alternative, the graphical display 124 can be configured to provide audio data or information to the operator.

In embodiments, one or more of the controller 114 and the graphical display 124 are configured to provide an operator of the intravascular catheter system 110 with a measurement of the duration of time that a catheter, such as the balloon catheter 118, is in the body of the patient during a medical procedure, such as a cryoablation procedure. This measurement of the duration is also referred to herein as the presence time of the catheter in the body of the patient during the medical procedure and the in-body treatment time of the medical procedure. In embodiments, the graphical display 124 displays the presence time or in-body treatment time, which more clearly defines the medical procedure. In embodiments, the presence time or in-body treatment time, as determined herein, can be used to improve planning of the medical procedure and/or reduce the cost of the medical procedure.

Figure 2:
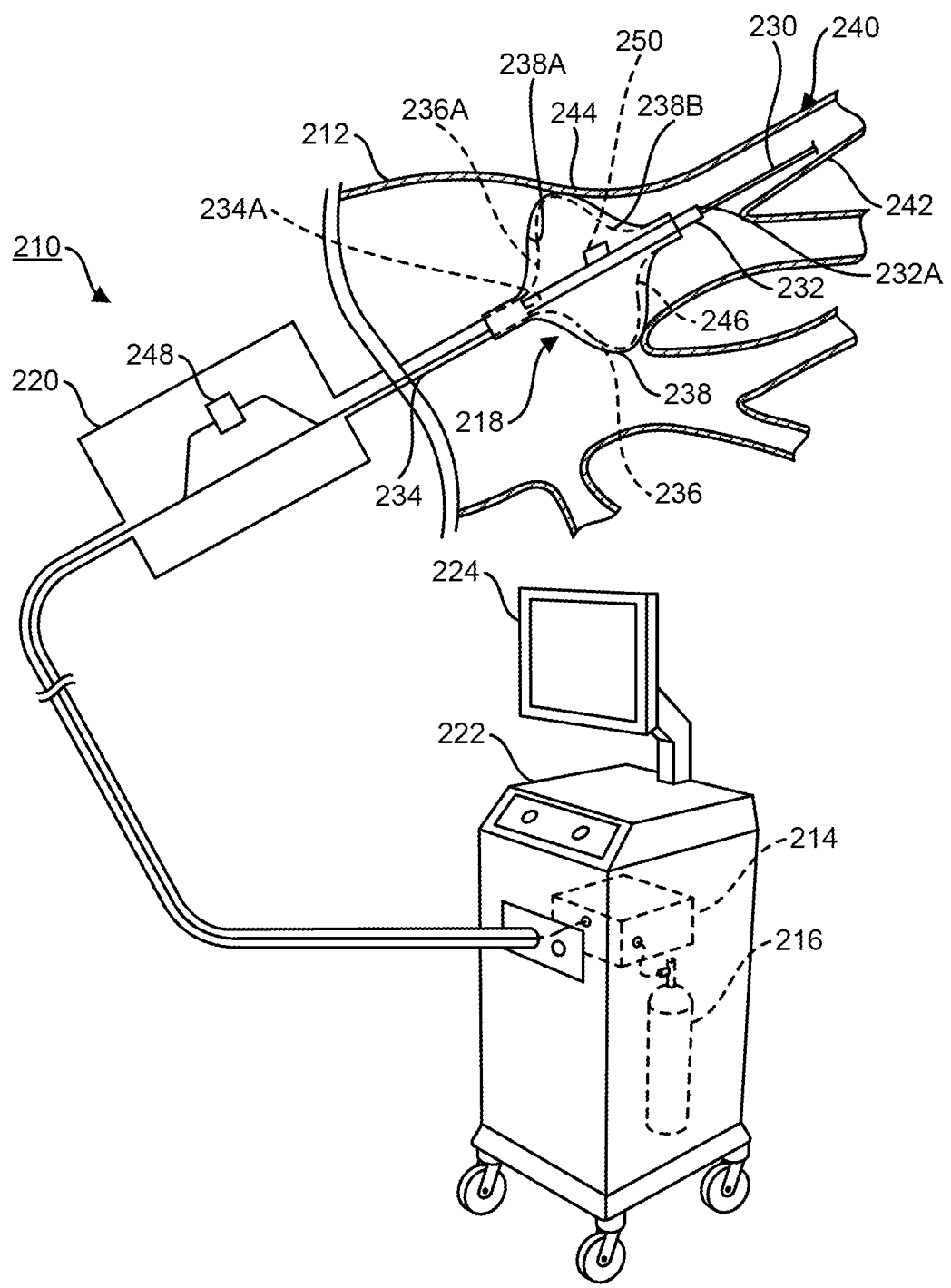
FIG. 2 is a simplified schematic side view illustrating a portion of the patient and a portion of the intravascular catheter system including the graphical display, according to embodiments of the disclosure.

FIG. 2 is a simplified schematic side view illustrating a portion of an intravascular catheter system 210 and a portion of a patient 212, according to embodiments of the disclosure. In embodiments, the intravascular catheter system 210 includes one or more of: a controller 214 (illustrated in dashed lines); a fluid source 216 (illustrated in dashed lines); a balloon catheter 218; a handle assembly 220; a control console 222; and a graphical display 224.

In some embodiments, the intravascular catheter system 210 is similar to the intravascular catheter system 110 (shown in FIG. 1). In some embodiments, one or more of the controller 214, the fluid source 216, the balloon catheter 218, the handle assembly 220, the control console 222, and the graphical display 224 are similar to the corresponding component in the intravascular catheter system 110 of the controller 114, the fluid source 116, the balloon catheter 118, the handle assembly 120, the control console 122, and the graphical display 124 (shown in FIG. 1).

The controller 214 is configured to control various functions of the intravascular catheter system 210. As shown in FIG. 2, in some embodiments, the controller 214 can be positioned substantially within the control console 222. Alternatively, at least a portion of the controller 214 can be positioned in one or more other locations within the intravascular catheter system 210, e.g., within the handle assembly 220. In some embodiments, the controller 214 can receive sensor output, also sometimes referred to herein as "data" or a "compilation of data", or other output from the balloon catheter 218, and can send the sensor output to the graphical display 224. Further, the controller 214 can control various functions of the remainder of the intravascular catheter system 210 based at least in part on data or other information received by the controller 214.

In various embodiments, the controller 214 (and in at least some embodiments the controller 114) can include at least one processor, e.g., at least one microprocessor, that executes software and/or firmware stored in memory of the controller 214. The software/firmware code contains instructions that, when executed by the processor, cause the controller 214 to perform the functions of the intravascular catheter system 210 described herein. The controller 214 may alternatively include one or more application-specific integrated circuits (ASICs), field-programmable gate arrays (FPGAs), digital signal processors (DSPs), hardwired logic, or combinations thereof. The controller 214 may receive information from a plurality of intravascular catheter system 210 components and feed the information, e.g., sensor data and user inputs from a user interface, into a control algorithm which determines at least one control parameter which may in part govern operation of the intravascular catheter system 210.

The design of the balloon catheter 218 can be varied to suit the design requirements of the intravascular catheter system 210. In this embodiment, the balloon catheter 218 includes one or more of a guidewire 230, a guidewire lumen 232, a catheter shaft 234, an inner balloon 236 and an outer balloon 238. It is recognized that the inner balloon 236 and the outer balloon 238 can also be referred to as a "first balloon" and a "second balloon", and that either balloon 236, 238 can be the first balloon or the second balloon. Alternatively, the balloon catheter 218 can be configured to include only a single balloon. It is also understood that the balloon catheter 218 can include other structures as well. However, for the sake of clarity, these other structures have been omitted from the figures.

As shown in FIG. 2, the balloon catheter 218 is configured to be positioned within the circulatory system 240 of the patient 212. The guidewire 230 and guidewire lumen 232 are inserted into a pulmonary vein 242 of the patient 212, and the catheter shaft 234 and the balloons 236, 238 are moved along the guidewire 230 and/or the guidewire lumen 232 to near an ostium 244 of the pulmonary vein 242. In embodiments, it is an object of the balloon catheter 218 to seal the pulmonary vein 242 so that blood flow is occluded. Only when occlusion is achieved does the cryothermic energy, e.g., of the cryogenic fluid 126 (shown in FIG. 1), cause tissue necrosis which, in turn, provides for electrically blocking aberrant electrical signals that trigger atrial fibrillation.

Additionally, as shown, the guidewire lumen 232 encircles at least a portion of the guidewire 230. During use, the guidewire 230 is inserted into the guidewire lumen 232 and can course through the guidewire lumen 232 and extend out of a distal end 232A of the guidewire lumen 232. In embodiments, the guidewire 230 can also include a mapping catheter (not shown) that maps electrocardiograms in the heart, and/or can provide information needed to position at least portions of the balloon catheter 218 within the patient 212.

In embodiments, the inner balloon 236 is positioned substantially, if not completely, within the outer balloon 238. The specific design of and materials used for each of the balloons 236, 238 can be varied. For example, in some non-exclusive embodiments, the balloons 236, 238 can be formed from one or more of various grades of polyether block amides (PEBA), polyurethane, polyethylene terephthalate (PET), nylon, and other co-polymers of these materials. Alternatively, the balloons 236, 238 can be formed from other suitable materials.

Additionally, in some embodiments, one end of the inner balloon 236 is bonded to a distal end 234A of the catheter shaft 234, and the other end of the inner balloon 236 is bonded near the distal end 232A of the guidewire lumen 232. Further, one end of the outer balloon 238 may be bonded to a neck of the inner balloon 236 or to the distal end 234A of the catheter shaft 234, and the other end of the outer balloon 238 may be bonded to the guidewire lumen 232. It is to be appreciated that a variety of bonding techniques can be used and include heat bonding and adhesive bonding. Additionally, it is further appreciated that in embodiments that include only a single balloon, the balloon can be secured to the catheter shaft 234 and the guidewire lumen 232 in a similar manner. Alternatively, the balloons 236, 238 can be secured to other suitable structures.

During use, the inner balloon 236 can be partially or fully inflated so that at least a portion of the inner balloon 236 expands against at least a portion of the outer balloon 238. Stated in another manner, during use of the balloon catheter 218, at least a portion of an outer surface 236A of the inner balloon 236 expands and is positioned substantially directly against a portion of an inner surface 238A of the outer balloon 238. At certain times during usage of the intravascular catheter system 210, the inner balloon 236 and the outer balloon 238 define an inter-balloon space 246, or gap, between the balloons 236, 238. The inter-balloon space 246 is illustrated between the inner balloon 236 and the outer balloon 238 in FIG. 2 for clarity, although it is to be understood that at certain times during usage of the intravascular catheter system 210, the inter-balloon space 246 has very little or no volume. As provided herein, once the inner balloon 236 is sufficiently inflated, an outer surface 238B of the outer balloon 238 can then be positioned within the circulatory system 240 of the patient 212 to abut and/or substantially form a seal with the ostium 244 of the pulmonary vein 242 to be treated.

The balloon catheter 218 includes one or more temperature sensors 250 (illustrated in dashed lines) for sensing the temperature of the balloon catheter 218. The one or more temperature sensors 250 sense the temperature of the balloon catheter 218 and provide signals indicating the sensed temperature to the intravascular catheter system 210. In embodiments, the one or more temperature sensors 250 can be situated at different locations on or in the balloon catheter 218. In some embodiments, as illustrated in FIG. 2, at least one of the one or more temperature sensors 250 is situated inside the inner balloon 236. Also, in some embodiments, as illustrated in FIG. 2, at least one of the one or more temperature sensors 250 is situated inside the inner balloon 236 and adjacent the guidewire lumen 232. In some embodiments, at least one of the one or more temperature sensors 250 is situated outside the inner balloon 236 and, in some embodiments, at least one of the one or more temperature sensors 250 is situated outside the outer balloon 238, such as adjacent the distal end 232A of the guidewire lumen 232 and/or adjacent the distal end 234A of the catheter shaft 234.

The design of the handle assembly 220 can vary. In embodiments, the handle assembly 220 can include circuitry 248 that can form a portion of the controller 214. In embodiments, the circuitry 248 can transmit the electrical signals, such as the signals from the one or more sensors 250, or otherwise provide data to the controller 214. In some embodiments, the circuitry 248 can include a printed circuit board having one or more integrated circuits, or any other suitable circuitry. In other embodiments, the circuitry 248 can be omitted, or can be included within the controller 214, which in various embodiments can be positioned outside of the handle assembly 220, e.g., within the control console 222.

In embodiments, the one or more temperature sensors 250 sense the temperature of the balloon catheter 218 and provide the signals indicating the sensed temperature to the intravascular catheter system 210, such as to the controller 214. A portion of the intravascular catheter system 10, such as the controller 214, is configured to determine the temperature of the balloon catheter 218 and the rate of change of the temperature of the balloon catheter 218 with respect to time from the signals provided by the one or more temperature sensors 250. In addition, a portion of the intravascular catheter system 10, such as the controller 214, is configured to obtain state information about the operational state of the medical procedure, such as the operational state of the cryoablation procedure. Using the temperature, rate of change, and/or state information, the intravascular catheter system 10 determines a measurement of the presence time or in-body treatment time of the balloon catheter 218 in the patient 212 during the medical procedure.

The graphical display 224 receives data or a compilation of data from the controller 214 and displays information about the medical procedure on the graphical display 224. In embodiments, the graphical display 224 is configured to provide the operator with various forms and types of information or data that can be used by the operator before, during, and after an ablation procedure. For example, in embodiments, the graphical display 224 is configured to provide the operator with the presence time or in-body treatment time of the balloon catheter 218 in the patient 212 during the medical procedure. Also, in some embodiments, the graphical display 224 is configured to provide the operator with an incrementing real-time count of the presence time or in-body treatment time of the balloon catheter 218 in the patient 212 during the medical procedure.

Figure 3:
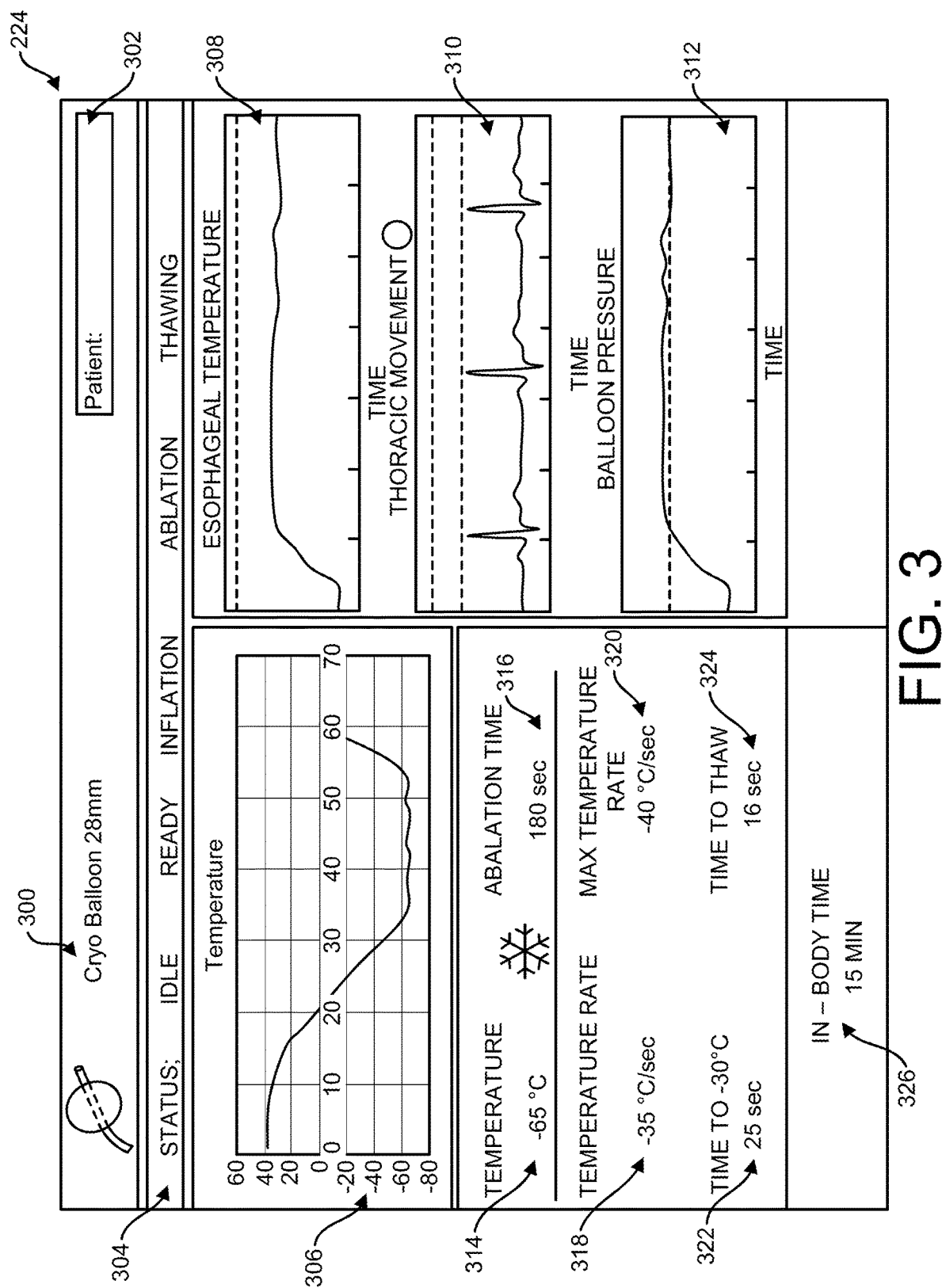
FIG. 3 is a diagram illustrating at least a portion of the graphical display shown in FIGS. 1 and 2, according to embodiments of the disclosure.

FIG. 3 is a diagram illustrating the graphical display 224 during a cryoablation procedure, according to embodiments of the disclosure. In embodiments, the graphical display 224 provides visual and/or audio information or data to the operator that pertains to the following: at 300, the type and/or size of the cryoablation balloon used in the cryoablation procedure; at 302, the patient's name or identification information; at 304, the operational state or status of the intravascular catheter system 210; at 306, a graph of the temperature of the balloon catheter 218 versus time during the cryoablation procedure; at 308, a graph of the esophageal temperature of the patient versus time during the cryoablation procedure; at 310, a graph of the thoracic movement of the patient indicative of operation of a phrenic nerve of the patient versus time during the cryoablation procedure; at 312, a graph of the balloon pressure versus time during the cryoablation procedure; at 314, a target ablation temperature or range or an actual ablation temperature or range; at 316, a measurement of the ablation time; at 318 and 320, a temperature rate change of the cryogenic fluid within the patient and the maximum temperature rate change of the cryogenic fluid within the patient, respectively; at 322, a time to reach a target temperature; at 324, a time for a temperature to increase from an actual ablation temperature to a preset thaw temperature; and, at 326, the presence time or in-body treatment time of the balloon catheter 218 in the patient 212 during the cryoablation procedure. In embodiments, at 326, the graphical display 224 is configured to provide the operator with an incrementing real-time count of the presence time or in-body treatment time of the balloon catheter 218 in the patient 212 during the cryoablation procedure. In embodiments, at 326, the graphical display 224 is configured to provide the final presence time or in-body treatment time, after the cryoablation procedure has been completed. In embodiments, at 326, the graphical display 224 is configured to provide the presence time or in-body treatment time in minutes. In embodiments, at 326, the graphical display 224 is configured to provide the presence time or in-body treatment time in minutes and seconds.

In some embodiments, the graphical display 224 provides visual and/or audio information or data to the operator that pertains to other parameters, such as one or more of the following: one or more ablation locations; a number of ablations at each location; a duration of each ablation at each location; a selection process for determining an ablation location; and a selection process to specify a temperature target and/or an ablation location or site. In addition, or in the alternative, the graphical display 224 can provide still other types of information or data that can be used by the operator before, during, and after the cryoablation procedure.

As illustrated in FIG. 3, the intravascular catheter system 210 provides multiple different operational states during the cryoablation procedure. The intravascular catheter system 210 indicates the current operational state or status of the system 210 via status indicators at 304. The different operational states include an idle state indicated at 330, a ready state indicated at 332, an inflation state indicated at 334, an ablation state indicated at 336, and a thawing state indicated at 338.

In operation, the intravascular catheter system 210 is activated or turned on and it enters the idle state, activating the idle state indicator at 330. In embodiments, during this time, the intravascular catheter system 210 may perform one or more self-diagnostic tests to verify that all systems are powered-up and functioning properly. If all systems are functioning properly, the intravascular catheter system 210 enters the ready state, indicating that it is ready for the next step in the medical procedure by activating the ready state indicator at 332. If all systems are not functioning properly, the intravascular catheter system 210 does not enter the ready state or activate the ready state indicator at 332. Instead, in some embodiments, the intravascular catheter system 210 indicates that all systems are not functioning properly with a visual indicator, such as a flashing light, and/or with an audio indicator, such as a buzzer. Also, after the cryoablation procedure has been completed, the intravascular catheter system 210 defaults to the idle state and/or the ready state, activating the idle state indicator at 330 and/or the ready state indicator at 332.

In embodiments, after the intravascular catheter system 210 enters the ready state and activates the ready state indicator at 332, medical personnel position the balloon catheter 218 in the patient 212, if this has not been previously done, for ablating tissue in the patient 212. The operator of the intravascular catheter system 210 then directs the system 210 to enter the inflation state, which activates the inflation state indicator at 334. During the inflation state, the balloon catheter 218 is inflated to expand the balloon catheter 218 against the tissue to be ablated. In embodiments, the inflation state is activated manually by the system operator or other medical personnel. For example, in embodiments, the system operator pushes a button on the control console 22 to enter the inflation state. Also, in embodiments, the cryogenic balloon 218 is inflated with any suitable fluid/gas, such as nitrogen or air.

After the balloon catheter 218 has been inflated, the intravascular catheter system 210 enters the ablation state and activates the ablation state indicator at 336. During the ablation state, a cryogenic fluid such as nitrous oxide or another suitable fluid is delivered under pressure to the inside of the balloon catheter 218. The cryogenic fluid causes the temperature of the balloon catheter 218 to drop and the extremely frigid balloon catheter 218 causes necrosis of the targeted tissue, thereby rendering the ablated tissue incapable of conducting unwanted electrical signals. In embodiments, the ablation state is at least partially, and maybe completely, controlled by the controller 14, such that the temperature of the balloon catheter 218 and/or the duration of the ablation is at least partially controlled by the intravascular catheter system 210. In embodiments, the ablation state is at least partially controlled by the operator of the intravascular catheter system 210, such that the temperature of the balloon catheter 218 and/or the duration of the ablation can be set or changed by the operator before the cryoablation procedure begins and/or during the cryoablation procedure. In embodiments, the ablation state is activated manually by the system operator or other medical personnel, such as by pushing a button on the control console 222 to enter the ablation state.

After the ablation state, the intravascular catheter system 210 enters the thawing state and activates the thawing state indicator at 338. During the thawing state, the cryogenic fluid is evacuated or removed from inside the balloon catheter 218 and the balloon catheter 218 thaws. In embodiments, the cryogenic fluid is replaced with fluid/gas, such as nitrogen or air, at room temperature during this part of the thawing stage to maintain inflation of the balloon catheter 218.

After the balloon catheter has thawed for a predetermined or set time and/or to a predetermined or set temperature, the balloon catheter 218 is deflated. The deflated balloon catheter 218 can then be removed from the patient 212. At this time, the cryogenic procedure has been completed and the intravascular catheter system 210 enters or is in the idle state and/or the ready state.

Figure 4:
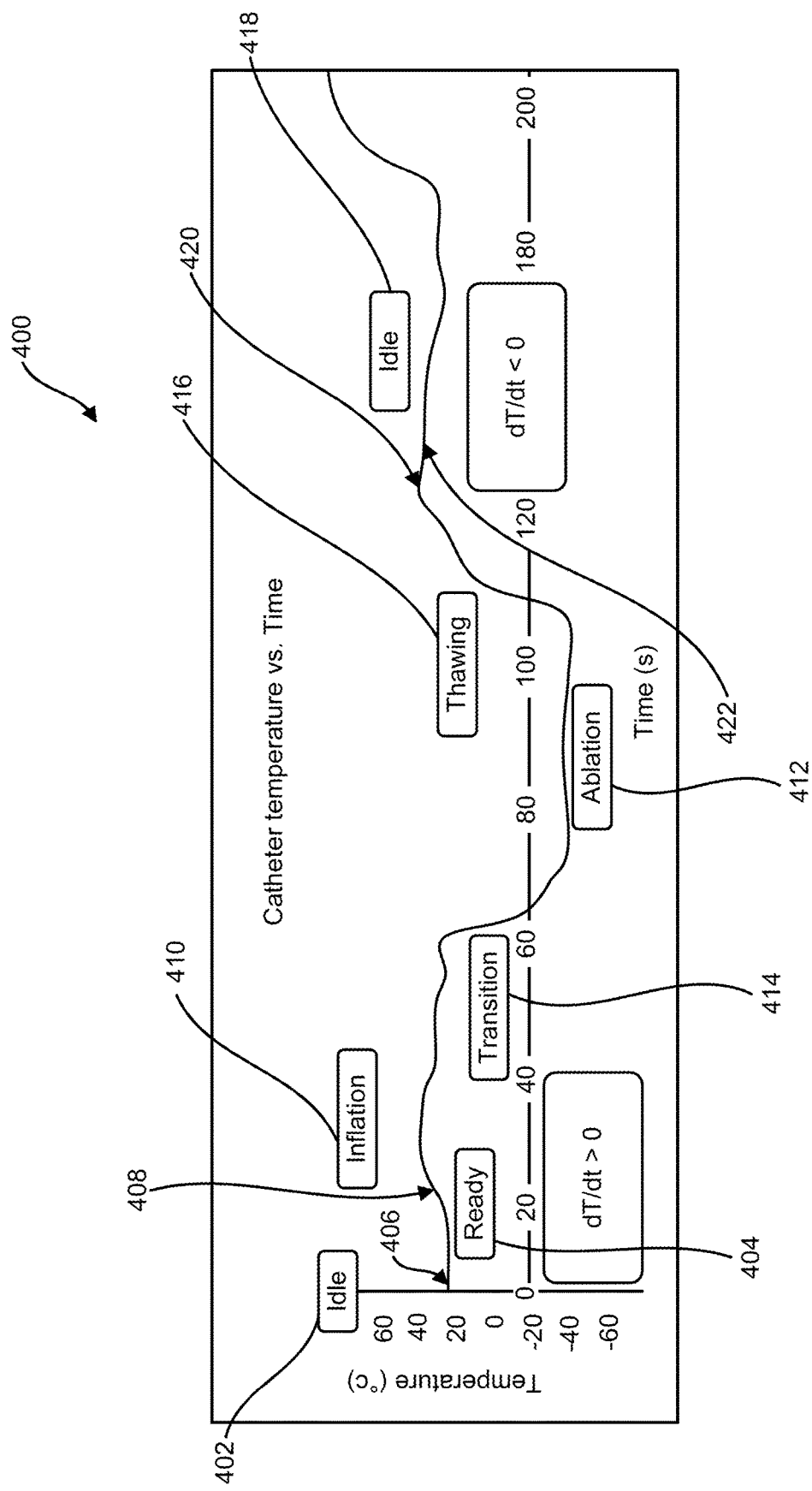
FIG. 4 is a graph illustrating the temperature of the catheter balloon versus time during an ablation procedure, according to embodiments of the disclosure.

FIG. 4 is a graph 400 illustrating the temperature of the catheter balloon 218 versus time during an ablation procedure, according to embodiments of the disclosure. The graph 400 is used herein to describe a determination of the presence time or in-body treatment time of the balloon catheter 218 in the patient 212. In embodiments, the controller 214 and/or other suitable portions of the intravascular catheter system 210 are configured to provide the determination of the presence time or in-body treatment time as described herein.

In the present example, the patient 212 is assumed to have a normal body temperature, such as about 37 degrees Centigrade (37 C) or 98.6 degrees Fahrenheit (98.6 F), and the room where the cryoablation procedure takes place, such as an operating room or another room, is at room temperature, such as 22 C or 71.6 F, which is below the normal body temperature.

At 402, the intravascular catheter system 210 is powered up and enters the idle state and, at 404, the intravascular catheter system 210 enters the ready state. At 406, the temperature of the balloon catheter 218 outside the patient 212 is measured to be room temperature, or about 22 C, i.e., the temperature of the balloon catheter 218 outside the patient 212 is less than the normal body temperature and the change in the temperature of the balloon catheter 218 with respect to time, dT/dt, outside the patient 212 tends to zero.

Next, at 408, the balloon catheter 218 is inserted into the patient 212 and the temperature of the balloon catheter 218 begins to slowly rise from room temperature of about 22 C toward the normal body temperature of about 37 C. This is the beginning of the presence time or in-body treatment time of the balloon catheter 218 in the body of the patient 212.

To detect this insertion of the balloon catheter 218 into the patient 212, a portion of the intravascular catheter system 210, such as the controller 214, receives the signals from the temperature sensor 250 and determines or calculates one or more of the temperature of the balloon catheter 218 and the change in temperature of the balloon catheter 218 with respect to time, dT/dt. From each of these measurements or from both measurements, the intravascular catheter system 210 determines whether the balloon catheter 218 has been inserted into the patient 212. After making this determination, if the balloon catheter 218 has been inserted into the patient 212 the intravascular catheter system 210 begins incrementing an in-body timer, IB time, such as once per second. Where, the IB time is the duration or presence time of the balloon catheter 218 in the body of the patient 212.

The IB time is displayed at 326 by the graphical display 224. In embodiments, IB time is displayed at 326 by the graphical display 224 in real-time, as it is incremented, as the presence time or in-body treatment time of the balloon catheter 218 in the patient 212 during the cryoablation procedure. In embodiments, IB time is displayed at 326 by the graphical display 224 in minutes in real-time, as it is incremented, as the presence time or in-body treatment time of the balloon catheter 218 in the patient 212 during the cryoablation procedure. In embodiments, IB time is displayed at 326 by the graphical display 224 in minutes and seconds in real-time, as it is incremented, as the presence time or in-body treatment time of the balloon catheter 218 in the patient 212 during the cryoablation procedure. In embodiments, IB time is displayed at 326 by the graphical display 224 as the total in-body treatment time, after the cryoablation procedure has been completed and IB time is no longer being incremented. In embodiments, IB time is displayed at 326 by the graphical display 224 in minutes as the total in-body treatment time, after the cryoablation procedure has been completed and IB time is no longer being incremented. In embodiments, IB time is displayed at 326 by the graphical display 224 in minutes and seconds as the total in-body treatment time, after the cryoablation procedure has been completed and IB time is no longer being incremented.

The intravascular catheter system 210 can determine that the balloon catheter 218 has been inserted into the patient 212 from the temperature of the balloon catheter 218 by comparing the measured temperature of the balloon catheter 218 to a predetermined threshold temperature, such as 32 C, that is between the room temperature of about 22 C and the normal body temperature of about 37 C. If the measured temperature of the balloon catheter 218 is greater than the threshold temperature, then it is determined that the balloon catheter 218 has been inserted into the body of the patient 212, and the normal body temperature of the patient is biasing or driving the measured temperature of the balloon catheter 218 higher than the threshold temperature.

Also, the intravascular catheter system 210 can determine that the balloon catheter 218 has been inserted into the patient 212 from the change in temperature of the balloon catheter 218 with respect to time, dT/dt, by determining that the change of temperature is positive and/or that the change in temperature is increasing at a rate that lies within a rate threshold range.

In some embodiments, the intravascular catheter system 210 determines whether or not the balloon catheter 218 has been inserted into the patient 212 by 1) comparing the measured temperature of the balloon catheter 218 to a predetermined threshold temperature as described above and by 2) determining that the change of temperature is positive and/or that the change in temperature is increasing at a rate that lies within a rate threshold range. In these embodiments, if both conditions are met, the intravascular catheter system 210 determines that the balloon catheter 218 has been inserted into the patient 212 and the intravascular catheter system 210 begins incrementing the in-body timer, IB time, such as once per second.

The intravascular catheter system 210 continues incrementing IB time during the inflation state at 410 and during the ablation state at 412. During the inflation state at 410, the temperature of the balloon catheter 218 may approach the normal body temperature. However, as soon as the intravascular catheter system 210 enters the ablation state at 412, the cryogenic fluid causes the balloon catheter 218 to drop.

During the transition portion 414 of the ablation state at 412, the temperature of the balloon catheter 218 drops below the predetermined threshold temperature of, for example, 32 C and during the remainder of the ablation state at 412 the temperature of the balloon catheter 218 remains below or less than the predetermined threshold temperature.

In embodiments, a portion of the intravascular catheter system 210, such as the controller 214, determines that the intravascular catheter system 210 is in the ablation state and that the temperature of the balloon catheter 218 is less than the predetermined threshold temperature, such as less than 32 C or negative. If both conditions are met, the intravascular catheter system 210 continues incrementing IB time.

During the thawing state at 416 and into the idle state (or ready state) at 418, the temperature of the balloon catheter 218 increases from less than the threshold temperature of, for example, 32 C to more than the threshold temperature. This is due to the normal body temperature biasing or driving the temperature of the balloon catheter 218 up to and higher than the threshold temperature.

In embodiments, during the thawing state at 416 and into the idle state (or ready state) at 418, the intravascular catheter system 210 calculates or determines the change of the temperature of the balloon catheter 218 with respect to time, dT/dt, and if this change is positive the intravascular catheter system 210 continues incrementing IB time. In embodiments, the determination of the change of the temperature of the balloon catheter 218 with respect to time can be done when the temperature of the balloon catheter 218 is: negative; less than the threshold temperature; and/or greater than the threshold temperature. In some embodiments, during the thawing state at 416 and into the idle state (or ready state) at 418, if the temperature of the balloon catheter 218 is less than the threshold temperature, than the intravascular catheter system 210 continues incrementing IB time.

During the idle state (or ready state) at 418, the temperature of the balloon catheter 218 may approach the normal body temperature at 420. However, as soon as the balloon catheter 218 is removed from the body of the patient 212, the temperature of the balloon catheter 218 begins to slowly drop at 422 toward room temperature. This is due to the room temperature being below the normal body temperature.

In embodiments, a portion of the intravascular catheter system 210, such as the controller 214, determines the change of the temperature of the balloon catheter 218 with respect to time, dT/dt, during the idle state (or ready state) 418 and if the change is negative, the intravascular catheter system 210 stops incrementing IB time. In embodiments, the controller 214, upon detecting a negative dT/dt, may determine whether the intravascular catheter system 210 is in either the ablation or thawing state, and if not, the intravascular catheter system 210 stops incrementing IP time.

The final IB time is the total presence time or in-body treatment time of the balloon catheter 218 in the patient 212 during the cryoablation procedure. This final IB time can be saved in a database and/or displayed on the graphical display 224.

By knowing the total presence time or in-body time of the balloon catheter 218 during the cryoablation procedure, medical personnel can determine items such as an ablation duration to total in-body time ratio, which can be used to help the medical personnel plan better procedures. Also, the total presence time or in-body time of the balloon catheter 218 can be used to better define costs of the medical procedure.

Figure 5:
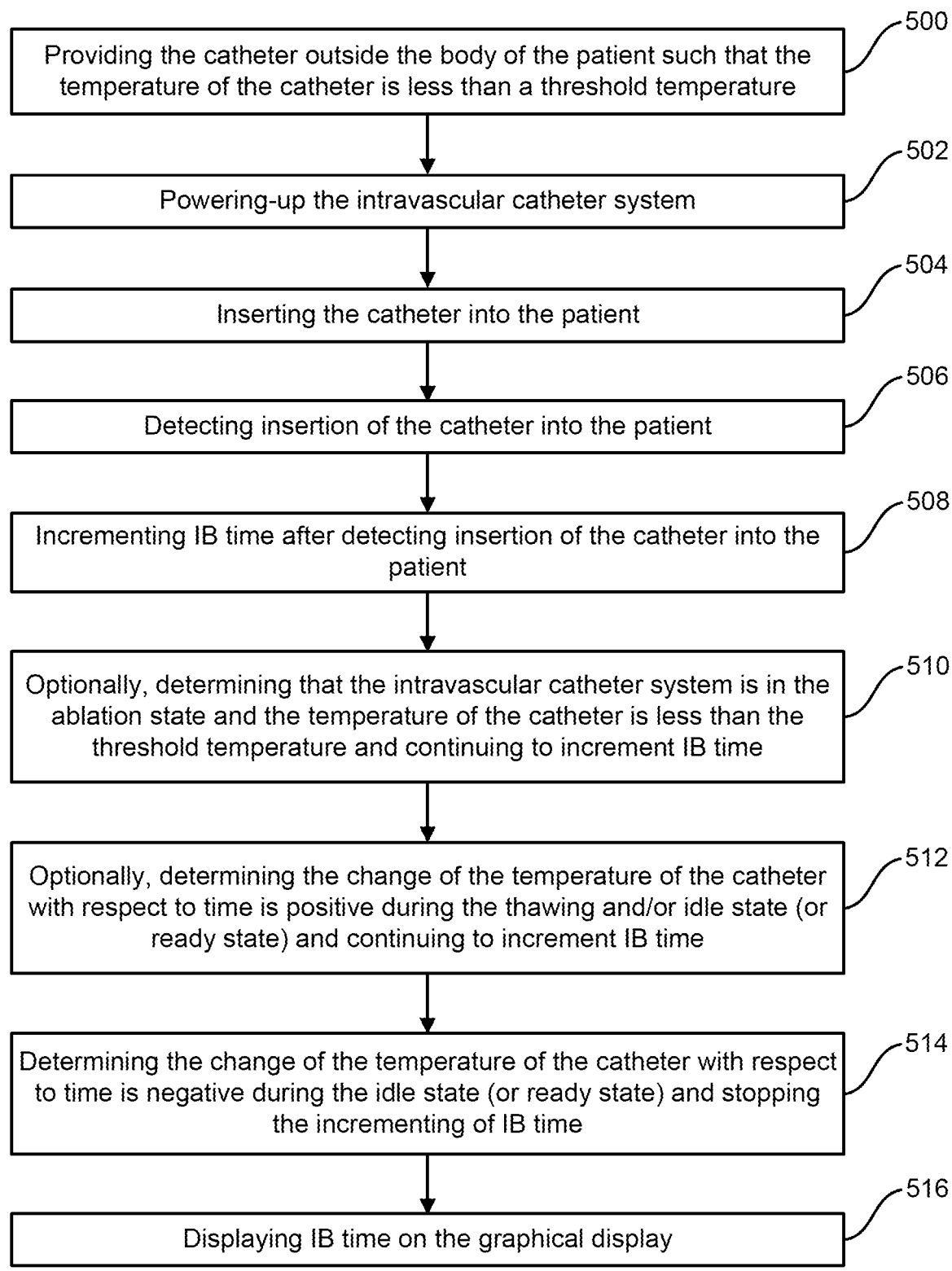
FIG. 5 is a flow chart diagram illustrating a method of determining the presence time of the intravascular catheter within the patient's body, according to embodiments of the disclosure.

FIG. 5 is a flow chart diagram illustrating a method of determining the presence time or in-body time of the balloon catheter 218 within the patient's body during a cryoablation procedure, according to embodiments of the disclosure. In embodiments, the controller 214 and/or other suitable portions of the intravascular catheter system 210 are configured to provide the method of determining the presence time or in-body time as described herein.

In the present example, the patient 212 is assumed to have a normal body temperature, such as about 37 C or 98.6 F, and the room where the cryoablation procedure takes place is at room temperature, such as 22 C or 71.6 F.

At 500, the method includes providing an intravascular catheter, such as the balloon catheter 218, outside the body of the patient 212, such that the temperature of the balloon catheter 218 is less than a threshold temperature that is between the room temperature of the room in which the cryoablation procedure takes place and the body temperature of the patient. In embodiments, providing the intravascular catheter includes providing the balloon catheter 218 outside the body of the patient 212, such that the temperature of the balloon catheter 218 is at least one of less than the body temperature of the patient and at room temperature. Also, with the balloon catheter 218 outside the body of the patient 212, the change in the temperature of the balloon catheter 218 with respect to time, dT/dt, tends to zero.

At 502, the method includes powering-up the intravascular catheter system 210, such that the intravascular catheter system 210 enters the idle state at 402 and then the ready state at 404. This can be done either before or after providing the intravascular catheter, such as the balloon catheter 218, outside the body of the patient 212.

At 504, after the intravascular catheter system 210 has entered the ready state at 404, the method includes inserting the balloon catheter 218 into the patient 212. After the balloon catheter 218 has been inserted into the patient 212, the temperature of the balloon catheter 218 begins to rise toward the normal body temperature of about 37 C. This is the beginning of the presence time or in-body treatment time (in-body time) of the balloon catheter 218 in the body of the patient 212.

At 506, the method includes detecting insertion of the balloon catheter 218 into the patient 212. Detecting insertion can be accomplished by determining one or more of a temperature of the balloon catheter 218 and the change in temperature of the balloon catheter 218 with respect to time, dT/dt.

In some embodiments, detecting insertion of the balloon catheter 218 into the patient 212 is accomplished by comparing the measured temperature of the balloon catheter 218 to a predetermined threshold temperature, such as 32 C. The predetermined threshold temperature is set to be between the room temperature and the normal body temperature. If the measured temperature of the balloon catheter 218 is greater than the threshold temperature, then it is determined that the balloon catheter 218 has been inserted into the body of the patient 212.

In some embodiments, detecting insertion of the balloon catheter 218 into the patient 212 is accomplished by determining the change in temperature of the balloon catheter 218 with respect to time, dT/dt. If the change of temperature is positive and/or the change in temperature is increasing at a rate that lies within a rate threshold range, then it is determined that the balloon catheter 218 has been inserted into the body of the patient 212.

In some embodiments, detecting insertion of the balloon catheter 218 into the patient 212 is accomplished by 1) comparing the measured temperature of the balloon catheter 218 to a predetermined threshold temperature as described above and 2) determining that the change of temperature of the balloon catheter 218 is positive and/or that the change in temperature of the balloon catheter 218 is increasing at a rate that lies within a rate threshold range. If both conditions are met, the intravascular catheter system 210 determines that the balloon catheter 218 has been inserted into the patient 212.

At 508, after the system determines that the balloon catheter 218 has been inserted into the patient 212, the method includes incrementing, by the intravascular catheter system 210, an in-body timer referred to as IB time. This incrementing is a continuous incrementing of the in-body timer to keep track of the time that has passed since the system determined that the balloon catheter 218 was inserted into the patient 212. In embodiments, IB time is incremented once per second. The IB time is the duration or presence time of the balloon catheter 218 in the body of the patient 212.

The intravascular catheter system 210 continues incrementing IB time during the inflation state at 410 and the ablation state at 412. During the inflation state at 410, the temperature of the balloon catheter 218 may approach the normal body temperature. However, as soon as the intravascular catheter system 210 enters the ablation state at 412, the cryogenic fluid passes into the balloon catheter 218 and the temperature of the balloon catheter 218 begins to drop. During the transition portion 414 of the ablation state at 412, the temperature of the balloon catheter 218 drops below the predetermined threshold temperature and during the remainder of the ablation state at 412 the temperature of the balloon catheter 218 remains below the predetermined threshold temperature.

Optionally, at 510, the method includes determining that the intravascular catheter system 210 is in the ablation state at 412 and that the temperature of the balloon catheter 218 is less than the predetermined threshold temperature, such as less than 32 C. If both conditions are met, the intravascular catheter system 210 continues incrementing IB time. After the ablation state at 412, the intravascular catheter system 210 enters the thawing state at 416 and/or the idle state (or ready state) at 418.

Optionally, at 512, the method includes determining the change of the temperature of the balloon catheter 218 with respect to time, dT/dt, during the thawing state at 416 and the idle state (or ready state) at 418. If this change is positive the intravascular catheter system 210 continues incrementing IB time. In some embodiments, the method includes comparing the temperature of the balloon catheter 218 to the threshold temperature during the thawing state at 416 and the idle state (or ready state) at 418, and if the temperature of the balloon catheter 218 is less than the threshold temperature then the intravascular catheter system 210 continues incrementing IB time.

During the idle state (or ready state) at 418, the temperature of the balloon catheter 218 may approach the normal body temperature. However, as soon as the balloon catheter 218 is removed from the body of the patient 212, the temperature of the balloon catheter 218 begins to slowly drop toward room temperature, due to the room temperature being below the normal body temperature.

At 514, the method further includes determining the change of the temperature of the balloon catheter 218 with respect to time, dT/dt, during the idle state (or ready state) 418 and if the change is negative, the intravascular catheter system 210 stops incrementing IB time. This final IB time is the total presence time or in-body treatment time of the balloon catheter 218 in the patient 212 during the cryoablation procedure. The final IB time can be saved in a database and/or displayed on the graphical display 224.

At 516, in embodiments, the method includes displaying the IB time at 326 on the graphical display 224. In some embodiments, the IB time is displayed in real-time, as it is incremented. In some embodiments, the IB time is displayed as the total in-body treatment time, after the cryoablation procedure has been completed and IB time is no longer being incremented. In some embodiments, the IB time is displayed in minutes. In some embodiments, the IB time is displayed in minutes and seconds.

As previously described, by knowing the total presence time or in-body time of the balloon catheter 218 during the cryoablation procedure, medical personnel can determine items such as an ablation duration to total in-body time ratio, which can be used to help the medical personnel plan better procedures. Also, the total presence time or in-body time of the balloon catheter 218 can be used to better define costs of the medical procedure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method of determining an in-body time of a medical device in a body of a patient during a cryoablation procedure, the method comprising:
   providing the medical device outside the body of the patient such that a temperature of the medical device is less than a threshold temperature that is between a room temperature of a room in which the cryoablation procedure takes place and a body temperature of the patient;
   detecting insertion of the medical device into the patient by one or more of measuring the temperature of the medical device and measuring the change of temperature of the medical device with respect to time;
   incrementing an in-body time counter to measure the in-body time of the medical device after detecting insertion of the medical device into the patient;
   detecting that the medical device has been removed from the patient by determining that the change of temperature of the medical device with respect to time is negative;
   stopping the incrementing of the in-body time counter in response to detecting that the medical device has been removed; and
   displaying the in-body time on a graphical display.

2. The method of claim 1, comprising:
   determining that a system is in an ablation state and the temperature of the medical device is less than the threshold temperature; and
   continuing the incrementing of the in-body time counter.

3. The method of claim 1, comprising:
  determining the change of the temperature of the medical device with respect to time is positive during one of a thawing state, an idle state, and a ready state of a system; and
  continuing the incrementing of the in-body time counter.

4. The method of claim 1, wherein detecting insertion of the medical device into the patient comprises comparing the temperature of the medical device to the threshold temperature, and if the temperature of the medical device is greater than the threshold temperature then the medical device has been inserted into the body of the patient.

5. The method of claim 1, wherein detecting insertion of the medical device into the patient further comprises determining the change in temperature of the medical device with respect to time, and if the change of temperature is positive and/or the change in temperature is increasing at a rate that lies within a rate threshold range.

6. The method of claim 1, wherein detecting insertion of the medical device into the patient comprises comparing the temperature of the medical device to the threshold temperature and determining the change in temperature of the medical device with respect to time, wherein 1) if the temperature of the medical device is greater than the threshold temperature and 2) the change of temperature is positive and/or the change in temperature is increasing at a rate that lies within a rate threshold range then the medical device has been inserted into the body of the patient.

7. The method of claim 1, wherein incrementing the in-body time counter comprises incrementing the in-body time counter at least once per second.

8. The method of claim 1, wherein detecting that the medical device has been removed from the patient comprises determining that a system is in an idle state or a ready state after an ablation state and the change of temperature of the medical device with respect to time is negative.

9. The method of claim 1, wherein displaying the in-body time on the graphical display comprises displaying the in-body time in real-time as the in-body time counter is incremented.

10. The method of claim 1, wherein displaying the in-body time on the graphical display comprises displaying the total in-body time after the incrementing of the in-body time counter has been stopped.

11. A method of determining a presence time of a catheter in a body of a patient during a cryoablation procedure, the method comprising:
  providing the catheter outside the body of the patient such that a temperature of the catheter is less than a threshold temperature that is between a room temperature of a room in which the cryoablation procedure takes place and a body temperature of the patient;
  powering-up an intravascular catheter system and entering a ready state of the intravascular catheter system;
  inserting the catheter into the patient;
  detecting insertion of the catheter into the patient during the ready state of the intravascular catheter system by one or more of measuring the temperature of the catheter and measuring the change of temperature of the catheter with respect to time;
  incrementing an in-body time counter at least once per second to measure the in-body time of the catheter after detecting insertion of the catheter into the patient;
  determining that the intravascular catheter system is in an ablation state and the temperature of the catheter is less than the threshold temperature and, in response, continuing the incrementing of the in-body time counter;
  determining the change of the temperature of the catheter with respect to time is positive during one of a thawing state, an idle state, and a ready state of the intravascular catheter system and, in response, continuing the incrementing of the in-body time counter;
  detecting that the catheter has been removed from the patient by determining that the change of temperature of the catheter with respect to time is negative during an idle state and/or a ready state after the ablation state;
  stopping the incrementing of the in-body time counter in response to detecting that the catheter has been removed; and
  displaying the in-body time on a graphical display.

12. The method of claim 11, wherein detecting insertion of the catheter into the patient comprises comparing the temperature of the catheter to the threshold temperature, and if the temperature of the catheter is greater than the threshold temperature then the catheter has been inserted into the body of the patient.

13. The method of claim 11, wherein detecting insertion of the catheter into the patient comprises determining the change in temperature of the catheter with respect to time, and if the change of temperature is positive and/or the change in temperature is increasing at a rate that lies within a rate threshold range then the catheter has been inserted into the body of the patient.

14. The method of claim 11, wherein detecting insertion of the catheter into the patient comprises comparing the temperature of the catheter to the threshold temperature and determining the change in temperature of the catheter with respect to time, wherein 1) if the temperature of the catheter is greater than the threshold temperature and 2) the change of temperature is positive and/or the change in temperature is increasing at a rate that lies within a rate threshold range then the catheter has been inserted into the body of the patient.

15. The method of claim 11, wherein displaying the in-body time on the graphical display comprises displaying the in-body time in real-time as the in-body time counter is incremented.

16. The method of claim 11, wherein displaying the in-body time on the graphical display comprises displaying the total in-body time after the incrementing of the in-body time counter has been stopped.

17. An intravascular catheter system, comprising:
  a catheter configured to be inserted into a body of a patient, the catheter including at least one temperature sensor configured to measure the temperature of the catheter;
  a controller configured to determine an in-body time of the catheter in the body of the patient during a cryoablation procedure, the controller configured to:
    receive signals from the at least one temperature sensor;
    detect insertion of the catheter into the patient by one or more of determining the temperature of the catheter and determining the change of temperature of the catheter with respect to time;
    increment an in-body time counter to measure the in-body time of the catheter after detecting insertion of the catheter into the patient;
    detect that the catheter has been removed from the patient by determining that the change of temperature of the catheter with respect to time is negative; and
    stop incrementing the in-body time counter in response to detecting that the catheter has been removed; and a graphical display configured to display the in-body time counter on the graphical display.

18. The system of claim 17, wherein the controller is configured to detect insertion of the catheter into the patient by one or more of 1) comparing the temperature of the catheter to a threshold temperature that is between a room temperature of a room in which the cryoablation procedure takes place and a body temperature of the patient and 2) determining the change of temperature is positive and/or the change in temperature is increasing at a rate that lies within a rate threshold range.

19. The system of claim 17, wherein the controller is configured to detect that the catheter has been removed from the patient by determining that the intravascular catheter system is in an idle state or a ready state after an ablation state and the change of temperature of the catheter with respect to time is negative.

20. The system of claim 17, wherein the graphical display displays one or more of the in-body time in real-time as the in-body time counter is incremented and the total in-body time after the incrementing of the in-body time counter has been stopped.

\* \* \* \* \*